(12) United States Patent
Pires et al.

(10) Patent No.: US 8,251,074 B2
(45) Date of Patent: *Aug. 28, 2012

(54) ADJUSTABLE APPLICATOR

(75) Inventors: Leo Clifford Pires, Basking Ridge, NJ (US); Roger Hwang, Maple (CA); Rahul Bose, New Delhi (IN); Abhisek Basak, New Delhi (IN); Shourya Asthana, New Delhi (IN); Koushik Kohli, Uttar Pradesh (IN); Santosh Mohapatra, New Delhi (IN)

(73) Assignee: ZEN Design Solutions Limited, Tsim Sha Tsui, Kowloon (HK)

( * ) Notice: Subject to any disclaimer, the term of this patent is extended or adjusted under 35 U.S.C. 154(b) by 0 days.

This patent is subject to a terminal disclaimer.

(21) Appl. No.: 12/975,333

(22) Filed: Dec. 21, 2010

(65) Prior Publication Data
US 2011/0088712 A1   Apr. 21, 2011

Related U.S. Application Data

(63) Continuation-in-part of application No. 12/363,117, filed on Jan. 30, 2009, which is a continuation-in-part of application No. 12/025,249, filed on Feb. 4, 2008, now abandoned.

(51) Int. Cl.
*A45D 40/26* (2006.01)
*A45D 33/00* (2006.01)
(52) U.S. Cl. ....................... 132/218; 401/130
(58) Field of Classification Search .................. 132/218, 132/317; 401/126–130, 176, 179, 101, 108; 206/571
See application file for complete search history.

(56) References Cited

U.S. PATENT DOCUMENTS

| | | | |
|---|---|---|---|
| 4,326,548 | A | 4/1982 | Wagner |
| 4,428,388 | A | 1/1984 | Cassai et al. |
| 4,598,723 | A | 7/1986 | Cole |
| 4,731,896 | A | 3/1988 | de La Tour |
| 5,137,038 | A | 8/1992 | Kingsford |
| 6,082,999 | A | 7/2000 | Tcherny et al. |
| 6,220,254 | B1 | 4/2001 | Gueret |
| 6,309,125 | B1 | 10/2001 | Peters |
| 6,497,235 | B2 | 12/2002 | Dorsa et al. |

(Continued)

FOREIGN PATENT DOCUMENTS
WO   WO 2007/117091 A1   10/2007

OTHER PUBLICATIONS

WO 2007/117091A Kim, HakChan A Deformable Mascara Brush, Oct. 18, 2007.*

(Continued)

*Primary Examiner* — Robyn Doan
(74) *Attorney, Agent, or Firm* — Patterson & Sheridan, LLP

(57) ABSTRACT

An adjustable applicator employed for application of a cosmetic or a care product such as for application of mascara, coloring strands of hair, for dental flossing or for applying pharmaceuticals or cleaning agents is provided. In one embodiment, an adjustable applicator includes an applicator element having a bore, a filament wherein the filament is housed inside the bore of the applicator element and a clasping means wherein the applicator element angularly deforms when a force is applied on the clasping means such that the angular deformation occurs on the radial axis of the applicator element. Also disclosed is a device for packaging and dispensing a substance that includes an adjustable applicator.

1 Claim, 17 Drawing Sheets

U.S. PATENT DOCUMENTS

| | | |
|---|---|---|
| 7,429,141 B2 | 9/2008 | Habatjou |
| 7,467,905 B2 | 12/2008 | Habatjou |
| 2002/0020425 A1 | 2/2002 | Dorsa et al. |
| 2004/0035437 A1 | 2/2004 | Gueret |
| 2004/0134507 A1 | 7/2004 | Gueret |
| 2004/0182410 A1 | 9/2004 | Gueret |
| 2006/0228157 A1 | 10/2006 | Dieudonat et al. |
| 2007/0025803 A1 | 2/2007 | Dieudonat |
| 2007/0221241 A1 | 9/2007 | Gueret |

OTHER PUBLICATIONS

PCT international search report and written opinion of PCT/US2009/062332 dated Jun. 11, 2010.

* cited by examiner

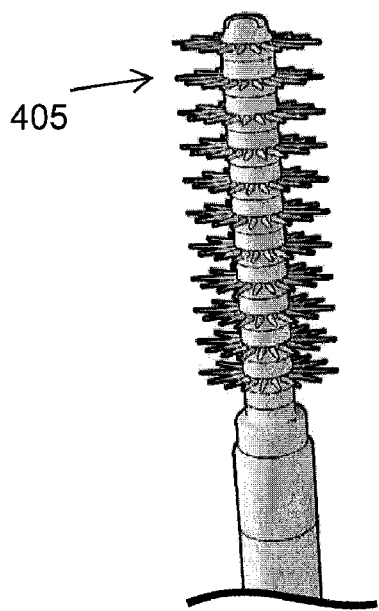
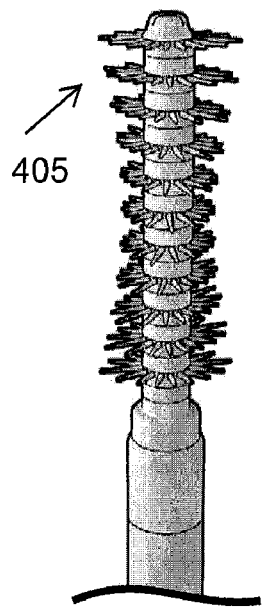
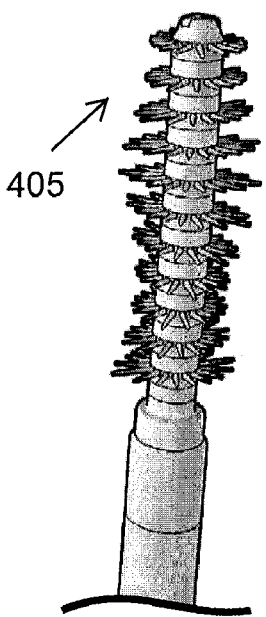
Fig. 17a     Fig. 17b     Fig. 17c
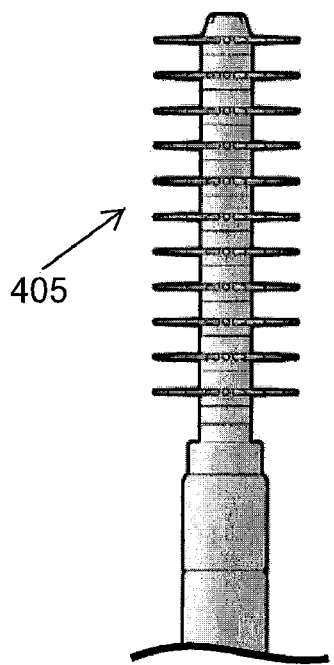
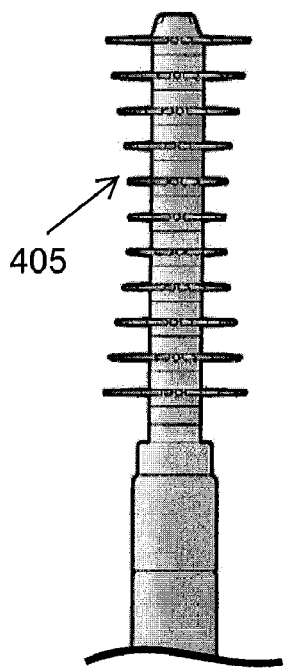
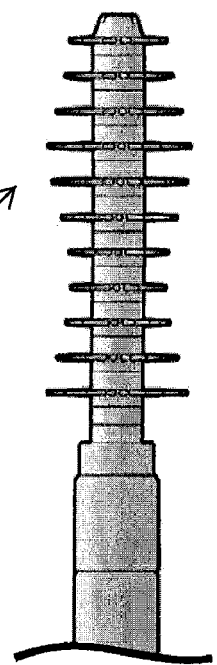
Fig. 18a     Fig. 18b     Fig. 18c

405

405

405

ADJUSTABLE APPLICATOR

CROSS-REFERENCE TO RELATED APPLICATION

This application is a continuation-in-part of U.S. patent application Ser. No. 12/363,117 filed Jan. 30, 2009, which is a continuation-in-part of U.S. patent application Ser. No. 12/025,249 filed Feb. 4, 2008 now abandoned, which are both incorporated by reference in its entirety.

BACKGROUND

1. Field of the Invention

Embodiments of the present invention generally relate to adjustable applicators. More particularly the invention relates to applicators that can be adjusted as per user's convenience for application of a cosmetic or a care product.

Applicators of the present invention can be employed in application of various products, such as for viscous cosmetics, for coloring strands of hair, and for dental flossing or for applying pharmaceuticals or cleaning agents.

2. Description of the Related Art

Various applicators for applying a substance are known. There are certain application areas where there is a requirement of curving the applicator as per user's convenience. Some such areas include application of mascara or in the cleaning of dental interstices. Majority of the existing applicators for such usages are pre-curved at a certain angle. For example U.S. Pat. No. 4,326,548 to Wagner discloses an oral hygiene tool comprising of a pen barrel shaped holder that carries a curved dental pick. Another example is that of U.S. Pat. No. 6,082,999 to Tcherny et. Al. which discloses a reusable flexible interdental device that has advantages of a toothpick and an interdental brush and also provides flexibility in two mutually perpendicular directions. However, the flexibility achieved is not controllable by the user. Therefore, there exists a need for a personal oral hygiene tool which can be used as per convenience by the user.

Also, mascara, an important make-up accessory used to darken and define eyelashes to accentuate the eyes, is difficult to apply because of the target area of application. The eyelashes offer a very small application area, while being soft, flexible, delicate and in close proximity to very sensitive eye tissue. Therefore, a mascara product would be liked by the consumers when a right kind of applicator is provided to them for easy application as the overall consumer experience depends on both the product and on the applicator used to apply it.

Mascara applicators such as twisted wire mascara brushes, curved mascara brushes and adjustable mascara applicators are known in the art. Curved mascara brushes permit contact of the brush with more eyelashes along a correspondingly curved eyelid. However, the rigid curved brush is a more difficult instrument to learn to use in the confines of the eye area, particularly the corners of the eye where a straight brush works better. Another drawback of pre-curved brush is that it is not readily adjustable to conform to a particular user's eyelid curvature. In addition, the curvature of the upper and lower eyelids is rarely the same and a brush curved to fit the upper lid will not properly fit the lower lid.

Adjustable mascara brushes are known in the prior art. It is known to provide adjustment of the angle of the brush or applicator relative to the applicator wand or handle as in U.S. Pat. No. 4,428,388 to Cassai et al. and the amount of brush exposed as in U.S. Pat. No. 4,598,723 to Cole.

U.S. Pat. No. 5,137,038 to Kingsford discloses an adjustable mascara applicator which can be adjusted by a user from straight to curved by the help of an extendable rod which is slidably disposed in the applicator wand. This rod may be straight to straighten a precurved applicator or curved so as to impart curvature to a straight applicator.

U.S. Pat. No. 6,309,125 to Andrea Peters discloses an adjustable mascara applicator that includes a brush attached to a bendable wand which is characterized by recovery memory in which it automatically assumes a predetermined bend angle in the absence of bending force.

While International Patent application WO 2007/117091A1 to Amorepacific Corporation, discloses an adjustable mascara brush that includes a brush stick provided in a cap, a brush provided at the end of the brush stick and an elevating bar which is connected to the brush stick in a manner of screw wherein the brush gets straightened when the elevating bar is lowered and the brush gets curved when the elevating bar is elevated up.

Although many of these prior art adjustable applicators are relevant with respect to the present invention, most of them use an additional component i.e. a rod that is either pre-bent or has a recovery memory. Moreover, none of the designs propose a mechanism by which the applicator element could be straightened or curved to varying degrees without the usage of additional component.

Therefore, there exists a need for an applicator that provides ease-of-use as well as is modifiable to adapt to the shape requirement of the user.

Further, there may also be a requirement by the user to lift and curl the eyelashes, which generally requires a different instrument such as a curler. However, it would be desirable that a single applicator is able to apply and lift and curl the lashes. Therefore, there is a need for an applicator that provides added function of lifting and curling the eyelashes.

SUMMARY

The present invention generally is an adjustable applicator employed for application of a cosmetic or a care product such as for application of mascara, coloring strands of hair, for dental flossing or for applying pharmaceuticals or cleaning agents. The use of adjustable applicator of the present invention for removal of make up products is also contemplated.

According to an embodiment of the invention, there is provided an applicator which employs an inventive mechanism to enable angular deformation of the applicator element to varying degrees of deformation.

In accordance with an embodiment of the invention, the adjustable applicator of the invention comprises of an applicator element and a filament. In the applicator element is provided a bore that houses the filament. Further, the filament is arranged to be movable inside the bore of the applicator element.

According to an embodiment of the invention the bore in the applicator element may be either centrally or non-centrally aligned.

According to yet another embodiment of the invention, the applicator element may be molded as a single piece from an elastically deformable material. The applicator element may be produced from an elastomer or any other elastic material allowing compression and expansion of the applicator element.

According to an embodiment of the invention, the filament may be made out of a material selected from a polymeric material and metals.

According to an embodiment of the invention, the filament is so arranged as to cause progressive modification in the shape of the applicator element. The filament facilitates adjustment of the angular deformation of the applicator element.

According to an embodiment of the invention the applicator element further comprises a biasing member arranged so as to assist the material memory of the applicator.

According to yet another embodiment of the invention, one end of the filament is connected to the distal end of the applicator element and the other end of the filament is attached to a clasping means such that when force is applied on the clasping means it causes tension along the axis of the filament which results in angular deformation of the applicator element. Further, the force applied to the clasping means is directly proportional to the deformation angle of the applicator element achieved. The filament may alternatively be connected by way of a locking arrangement with the distal end of the applicator element thereby guiding the movement of the applicator. For example, when the filament is in a stretched state it causes the applicator to be bent while when it is in relaxed state it guides the applicator to come back to its straight position.

According to an embodiment of the invention the clasping means may be provided at the proximal end of the filament itself. Alternatively, the filament may be engaged with another element having clasping or any other suitable means for application of force. Further, the mode of application of force on the clasping means could be manual, mechanical, magnetic, electrical or any other suitable mode.

According to an embodiment of the invention the applicator element may have a substantially circular outside cross-section, but the case in which the deformable applicator element has a cross-section of different shape, such as polygonal, is also contemplated by this invention.

According to yet another embodiment of the invention, the filament may be fixed tautly at both the ends of the applicator element such that the angular deformation in the applicator element is caused by application of force along the axis of the applicator.

Independently or in combination with the above, exemplary embodiments of the invention provide a device for packaging and dispensing a substance, for example, a cosmetic, comprising an applicator as defined above. The device may comprise a receptacle and an adjustable applicator. The adjustable applicator in such a device may comprise a gripping member, a stem having a cavity and an applicator element wherein the stem may be connected to the applicator element at one end and to the gripping member at another end. The said device may also include a wiper member. The gripping member may comprise a cap for closing the receptacle and a manipulating means for adjusting the angular deformation of the applicator element. The said manipulating means could be connected to a movable member present inside the cap in such a way that its rotational movement with respect to the cap is restricted while translational movement is allowed and said movable member is connected to the filament in the applicator element.

According to another embodiment of the invention the movable member of the packaging device may be connected to the filament via another filament that passes through the cavity inside the stem and hooks up the filament of the applicator. In such a case, the force provided by the manipulating means effects synchronous movement of both the filament in the stem as well as the filament in the applicator with respect to the gripping member thereby adjusting the angular deformation of the applicator element.

According to yet another embodiment of the invention, the adjustable applicator may comprise a stem connected to the applicator element at one end and a gripping member provided at another end of the stem. The stem may be hollow from inside. The gripping member may comprise a handle member and a manipulating means for adjusting the angular deformation of the applicator element. The said manipulating means could be connected to a movable member present inside the handle in such a way that its rotational movement with respect to the handle is restricted while translational movement is allowed and said movable member is directly connected to the filament that passes through the cavity in the stem to the applicator element. In a further embodiment, the movable member may also be connected to the filament via a separate filament that passes through the cavity inside the stem and hooks up the filament of the applicator member. In such a case, the force provided by the manipulating means effects synchronous movement of both the filament in the stem as well as the filament in the applicator with respect to the handle for adjusting the angular deformation of the applicator element.

According to an embodiment of the invention, there is provided an adjustable applicator wherein the user has more control over the curved angle achieved in the applicator. Further, a constant rigidity of the applicator is provided as no additional component is inserted or withdrawn to achieve the straight or curved shape.

According to another embodiment of the invention, the applicator element is capable of being used for application of a care product such as a dental floss or in a cosmetic product such as mascara. Further, the adjustable applicator could also be used for removal of a cosmetic product such as mascara.

According to yet another embodiment of the invention there is provided an applicator which employs an inventive mechanism to enable radially-angular deformation of the applicator element to varying degrees of deformation. The radially angular deformation being defined herein as the angular deformation occurring on the radial axis of the applicator element. Further, the deformation may be regular or irregular. Alternatively, the deformation in the applicator may follow a helical path.

According to yet another embodiment of the invention the adjustable applicator comprises an applicator element and a filament. In the applicator element is provided a bore that houses the filament such that the filament is arranged to be movable inside the bore of the applicator element. The bore in the applicator element may be either centrally or non-centrally aligned. The applicator element may be molded as a single piece from an elastically deformable material. The applicator element may be produced from an elastomer or any other elastic material allowing radially-angular deformation of the applicator element.

According to an embodiment of the invention, the filament may be made out of a material selected from a polymeric material and metals.

According to an embodiment of the invention, the filament is so arranged as to cause progressive modification in the shape of the applicator element, there occurs a progressive decrease or increase in the angle of deformation of the applicator element. The filament facilitates adjustment of the radially-angular deformation of the applicator element. The radially-angular deformation may be distributed evenly throughout the applicator element i.e. the angular gap is maintained evenly in the body of the applicator element. As an exemplary embodiment the radially-angular deformation in the applicator element may be such that there occurs twisting of the body of the applicator element. Alternatively, the angular deformation may be irregular or uneven in the body of the applicator element. When the applicator element is a mascara brush, the angular deformation in the applicator element helps in lifting and curling of the eyelashes.

According to an embodiment of the invention the applicator element further comprises a biasing member arranged so as to assist the material memory of the applicator.

According to yet another embodiment of the invention, one end of the filament is connected to the distal end of the applicator element and the other end of the filament is attached to a clasping means such that when force is applied on the clasping means it causes tension along the radial axis of the filament which results in angular deformation of the applicator element. Further, the force applied to the clasping means is directly proportional to the deformation angle of the applicator element achieved. The filament may alternatively be connected by way of a locking arrangement with the distal end of the applicator element thereby guiding the movement of the applicator. For example, when the filament is in a stretched state it causes the applicator to be angularly deformed while when it is in relaxed state it guides the applicator to come back to its straight position.

According to an embodiment of the invention the clasping means may be provided at the proximal end of the filament itself. Alternatively, the filament may be engaged with another element having clasping or any other suitable means for application of force. Further, the mode of application of force on the clasping means could be manual, mechanical, magnetic, electrical or any other suitable mode.

According to an embodiment of the invention the applicator element may have a substantially circular outside cross-section, but the case in which the deformable applicator element has a cross-section of different shape, such as polygonal, is also contemplated by this invention.

According to yet another embodiment of the invention, the filament may be fixed tautly at both the ends of the applicator element such that the angular deformation in the applicator element is caused by application of force along the axis of the applicator.

Independently or in combination with the above, exemplary embodiments of the invention provide a device for packaging and dispensing a substance, for example, a cosmetic, comprising an applicator as defined above. The device may comprise a receptacle and an adjustable applicator. The adjustable applicator in such a device may comprise a gripping member, a stem having a cavity and an applicator element wherein the stem may be connected to the applicator element at one end and to the gripping member at another end. The said device may also include a wiper member. The gripping member may comprise a cap for closing the receptacle and a manipulating means for adjusting the angular deformation of the applicator element. The said manipulating means could be connected to an inner rod present inside the cap in such a way that its rotational movement with respect to the cap is allowed and said inner rod is further connected to the filament in the applicator element.

According to yet another embodiment of the invention, the adjustable applicator may comprise a stem connected to the applicator element at one end and a gripping member provided at another end of the stem. The stem may be hollow from inside. The gripping member may comprise a handle member and a manipulating means for adjusting the angular deformation of the applicator element. The said manipulating means could be connected to an inner rod present inside the handle in such a way that its rotational movement with respect to the handle is allowed and said inner rod may be in the form of a filament that passes through the cavity in the stem and connects to the applicator element. In a further embodiment, the inner rod may be connected to the applicator filament and hooks up the filament of the applicator member. In such a case, the force provided by the manipulating means effects synchronous movement of both the inner rod in the stem as well as the filament in the applicator with respect to the handle for adjusting the angular deformation of the applicator element.

According to an embodiment of the invention, there is provided an adjustable applicator wherein the user has more control over the angular deformation achieved in the applicator. Further, a constant rigidity of the applicator is provided as no additional component is inserted or withdrawn to achieve the straight or angularly deformed shape.

These and further aspects which will be apparent to the expert of the art are attained by an adjustable applicator in accordance with the main claim.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 17a is an isometric view of an adjustable applicator according to another embodiment of the invention;

FIG. 17b is an isometric view of the adjustable applicator of FIG. 17a showing the applicator as seen upon 180 degree radially-angular deformation;

FIG. 17c is an isometric view of the adjustable applicator of FIG. 17a showing the applicator as seen upon 360 degree radially-angular deformation;

FIG. 18a is a front view of the adjustable applicator of FIG. 17a;

FIG. 18b is a front view of the adjustable applicator of FIG. 17a showing the applicator as seen upon 180 degree radially-angular deformation;

FIG. 18c is an isometric view of the adjustable applicator of FIG. 17a showing the applicator as seen upon 360 degree radially-angular deformation;

FIG. 19a is a top view of the adjustable applicator of FIG. 17a;

Figure 1:
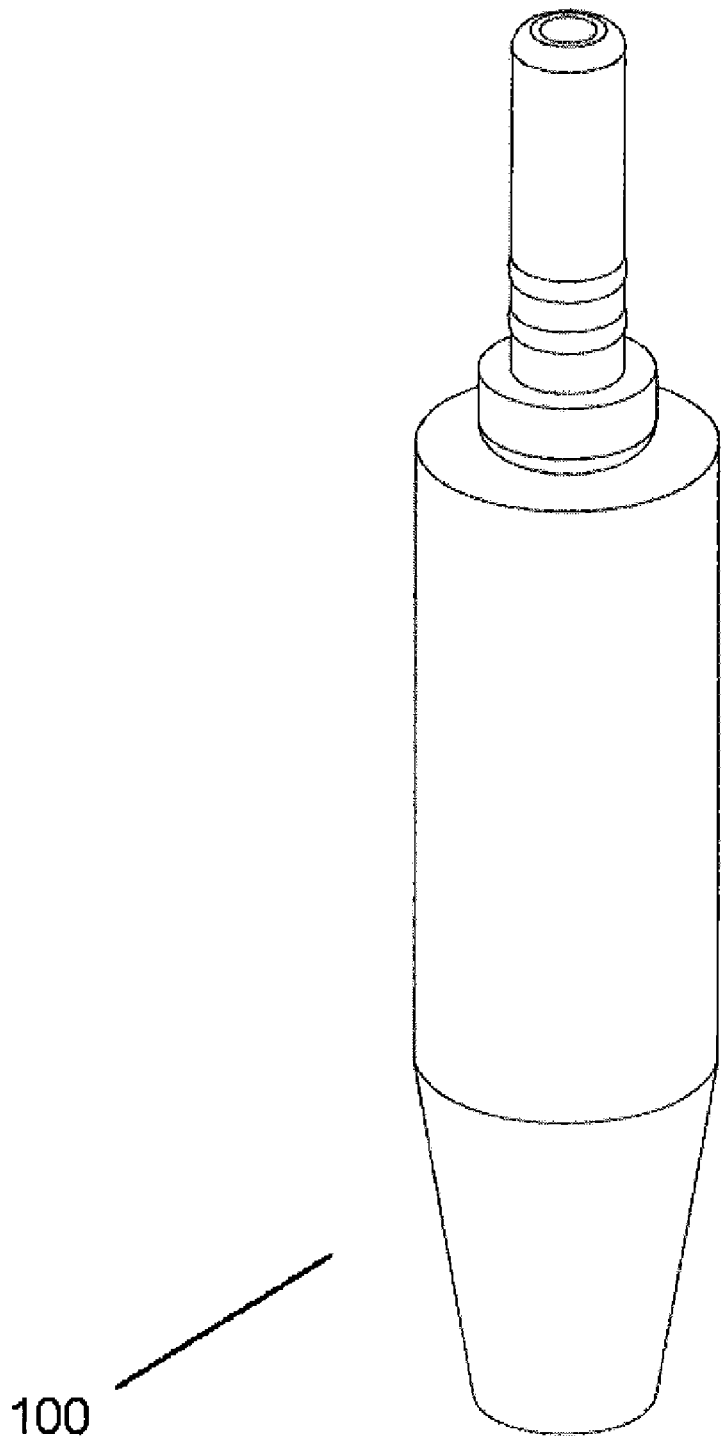
FIG. 1 illustrates an isometric view of the applicator according to an embodiment of the invention.

To facilitate understanding, identical reference numerals have been used, where possible, to designate identical elements that are common to the figures. It is to be noted, however, that the appended drawings illustrate only typical embodiments of this invention and are therefore not to be considered limiting of its scope, for the invention may admit to other equally effective embodiments.

DETAILED DESCRIPTION

Figure 2:
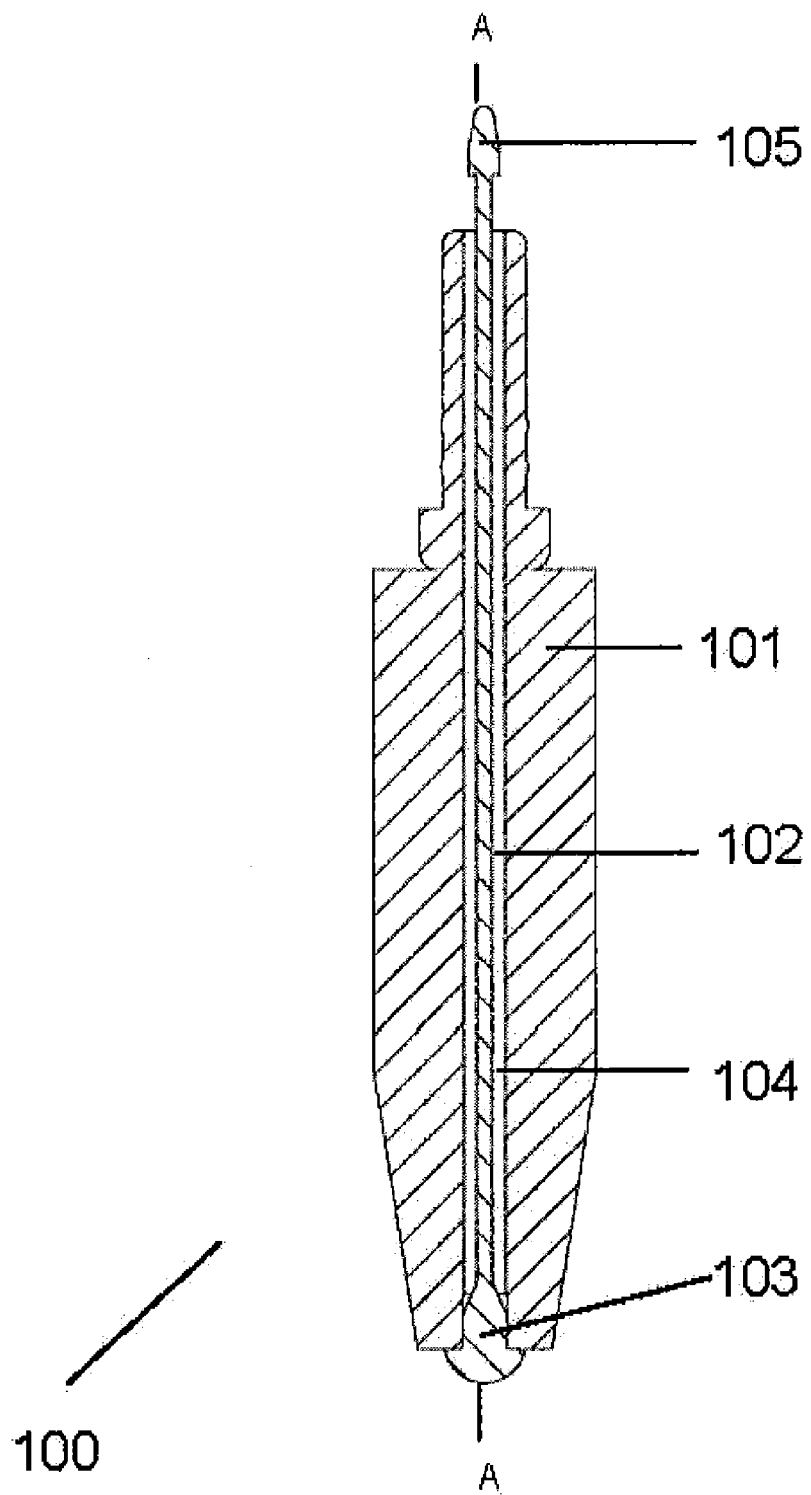
FIG. 2 is a cross sectional view of the applicator taken along the line A-A of FIG. 1
Figure 3:
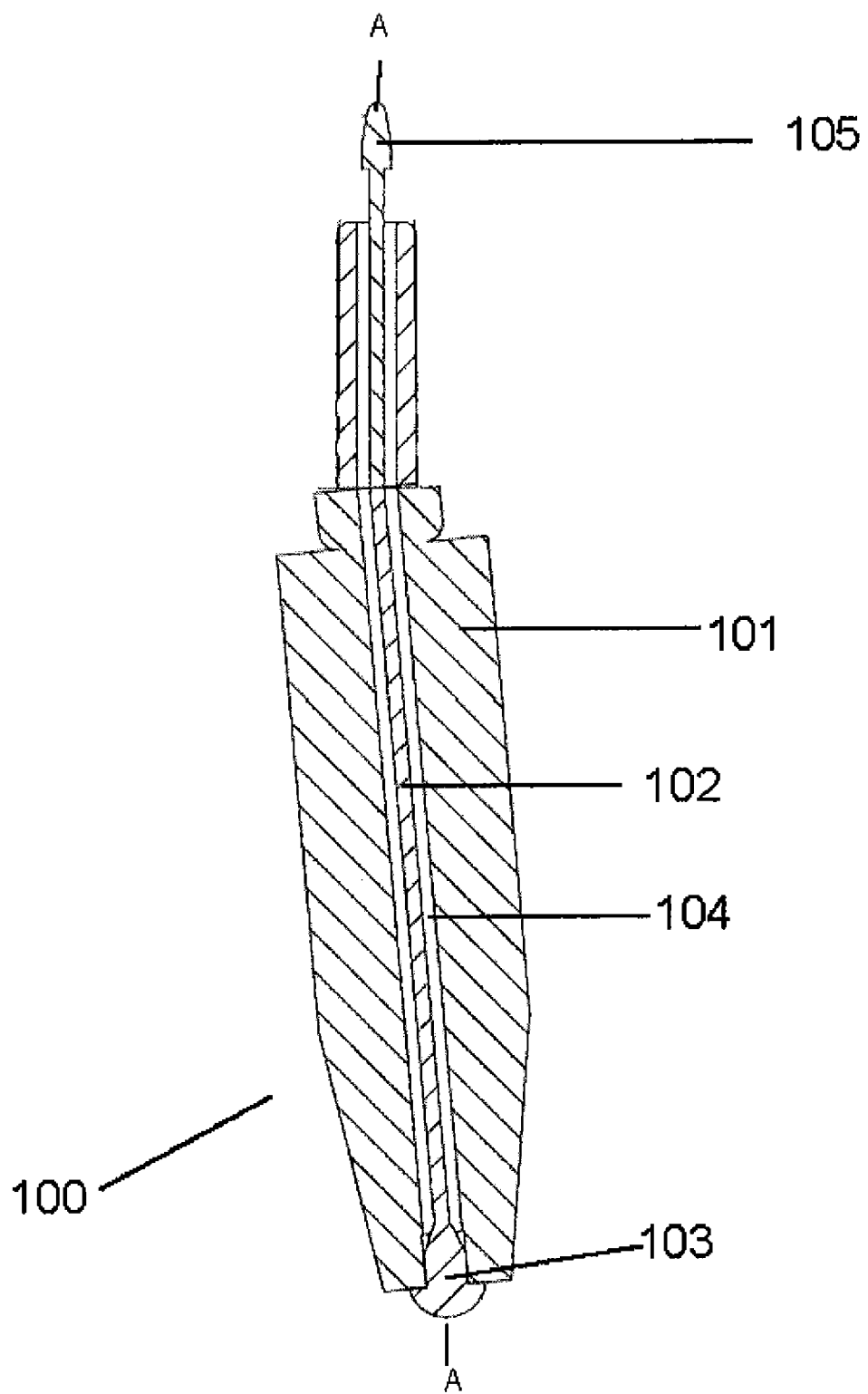
FIG. 3 is a cross sectional view of the applicator in curved position taken along the line A-A of FIG. 1.

The adjustable applicator according to one embodiment of the present invention is shown in FIGS. 1 to 3.

FIG. 1 is one embodiment of the present invention showing the adjustable applicator 100. The adjustable applicator 100 of the invention comprises of an applicator element 101 and a filament 102. In the applicator element 101 is a bore 104 housing the filament 102. The bore 104 may either be centrally or non-centrally aligned. The filament 102 is arranged to be movable inside the bore 104 of the applicator element 101. The applicator element 101 may be produced from an elastomer or any other elastic material allowing compression and expansion of the applicator. Further, the filament 102 may be made out of a material selected from a polymeric material and metals. The filament 102 is so arranged as to cause progressive angular deformation of the applicator element 101.

As shown in FIGS. 2 and 3, one end of the filament 102 is connected at a distal end 103 of the applicator 100 and the other end of the filament 102 is attached to a clasping means 105 such that when force is applied on the clasping means 105 it causes tension along the axis of the filament 102, which results in angular deformation of the applicator element 101 as is illustrated in FIG. 3. Further, the force applied on the filament 102 is directly proportional to the deformation angle of the applicator element 101 achieved. The mode of application of force on the clasping means 105 could be manual, mechanical, magnetic, electrical or any other suitable mode to cause tension along the axis of the filament 102. Moreover, the applicator element 101 may have a substantially circular outside cross-section, but the case in which the deformable applicator element 101 has a cross-section of different shape, such as polygonal, is also contemplated by this invention. Further, the applicator element may further comprise of a biasing member arranged so as to assist the material memory of the applicator element.

Figure 4:
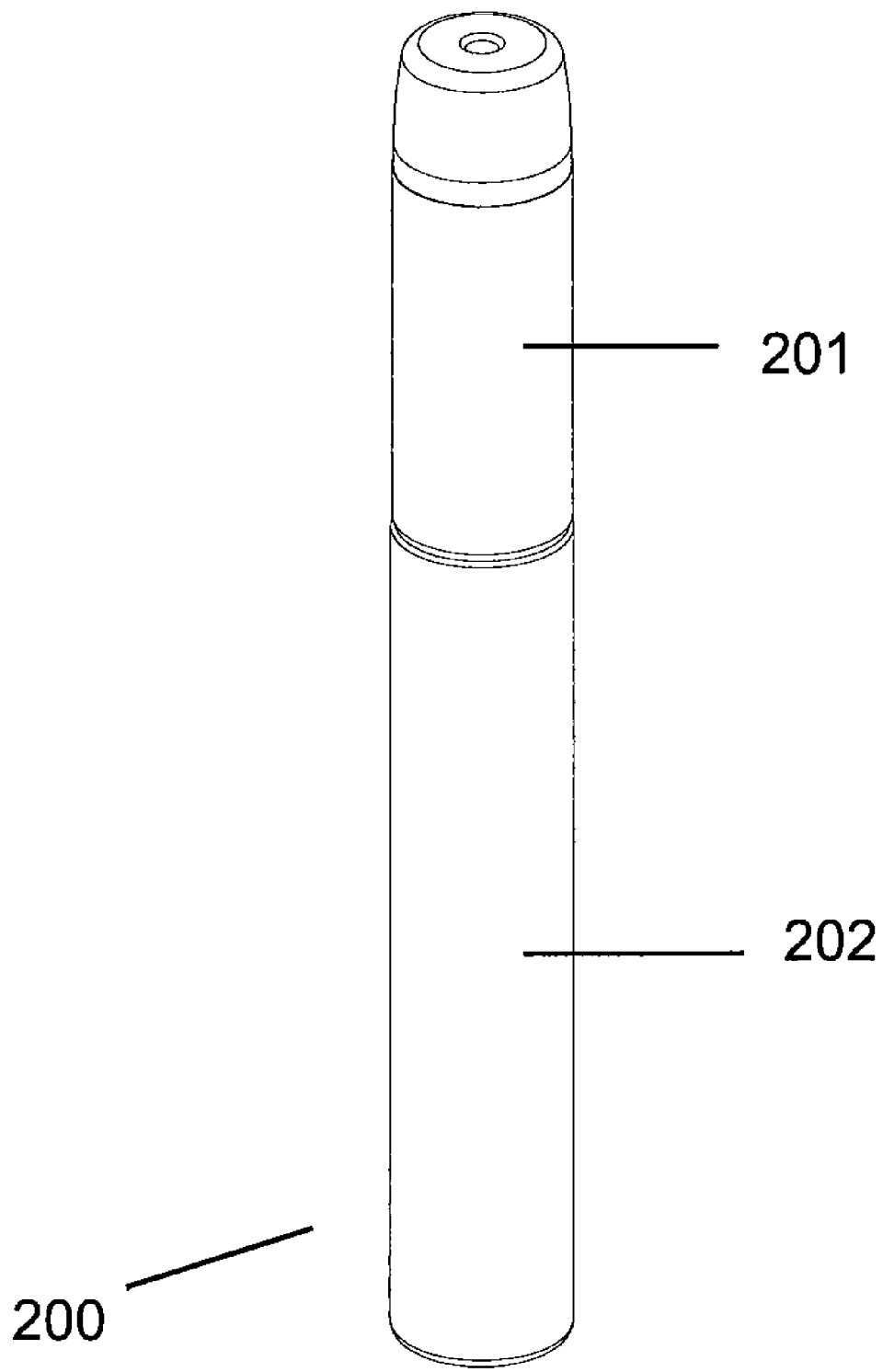
FIG. 4 illustrates an isometric view of the device comprising the adjustable applicator according to one embodiment of the present invention.
Figure 5:
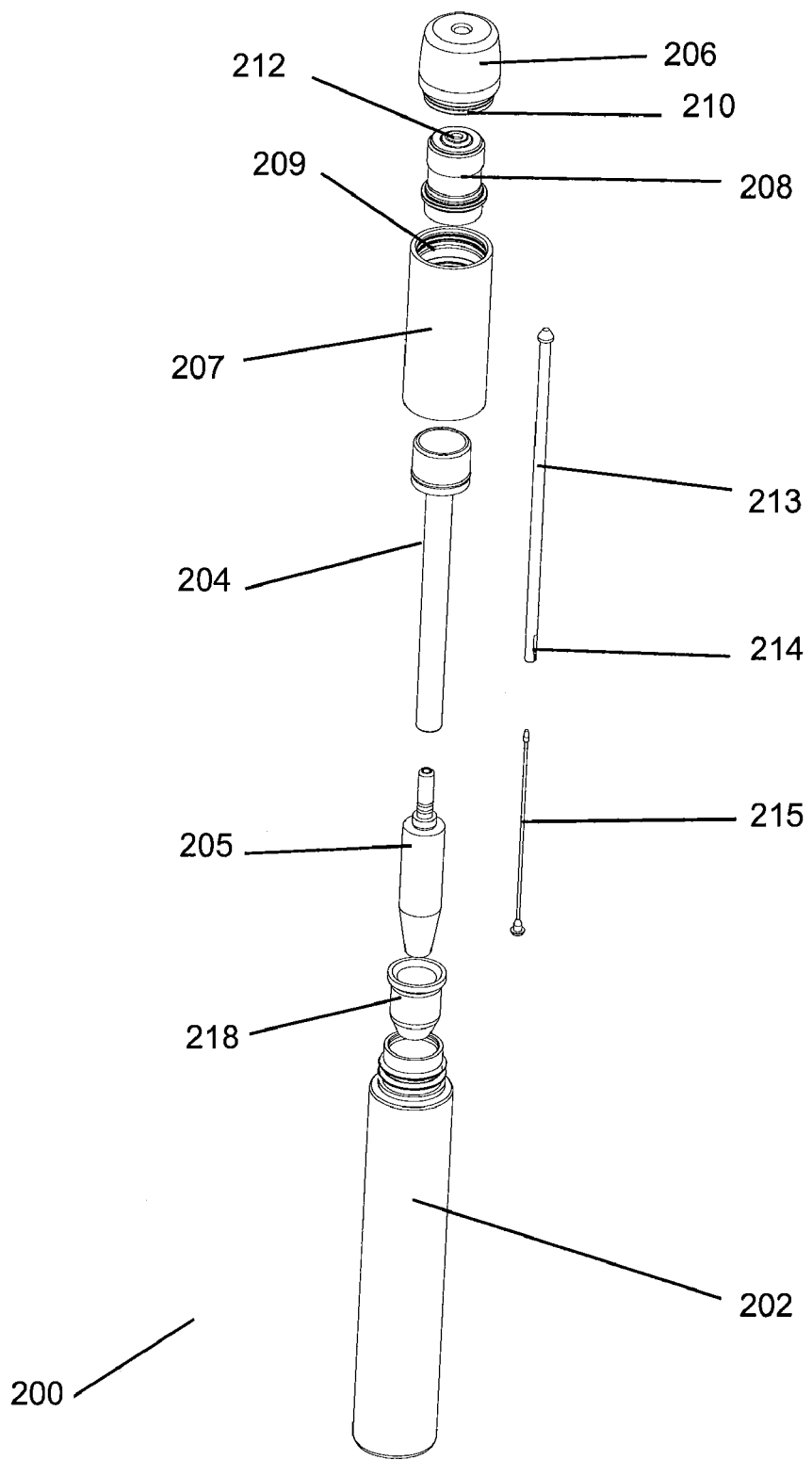
FIG. 5 illustrates an exploded view of the device of FIG. 4.
Figure 6:
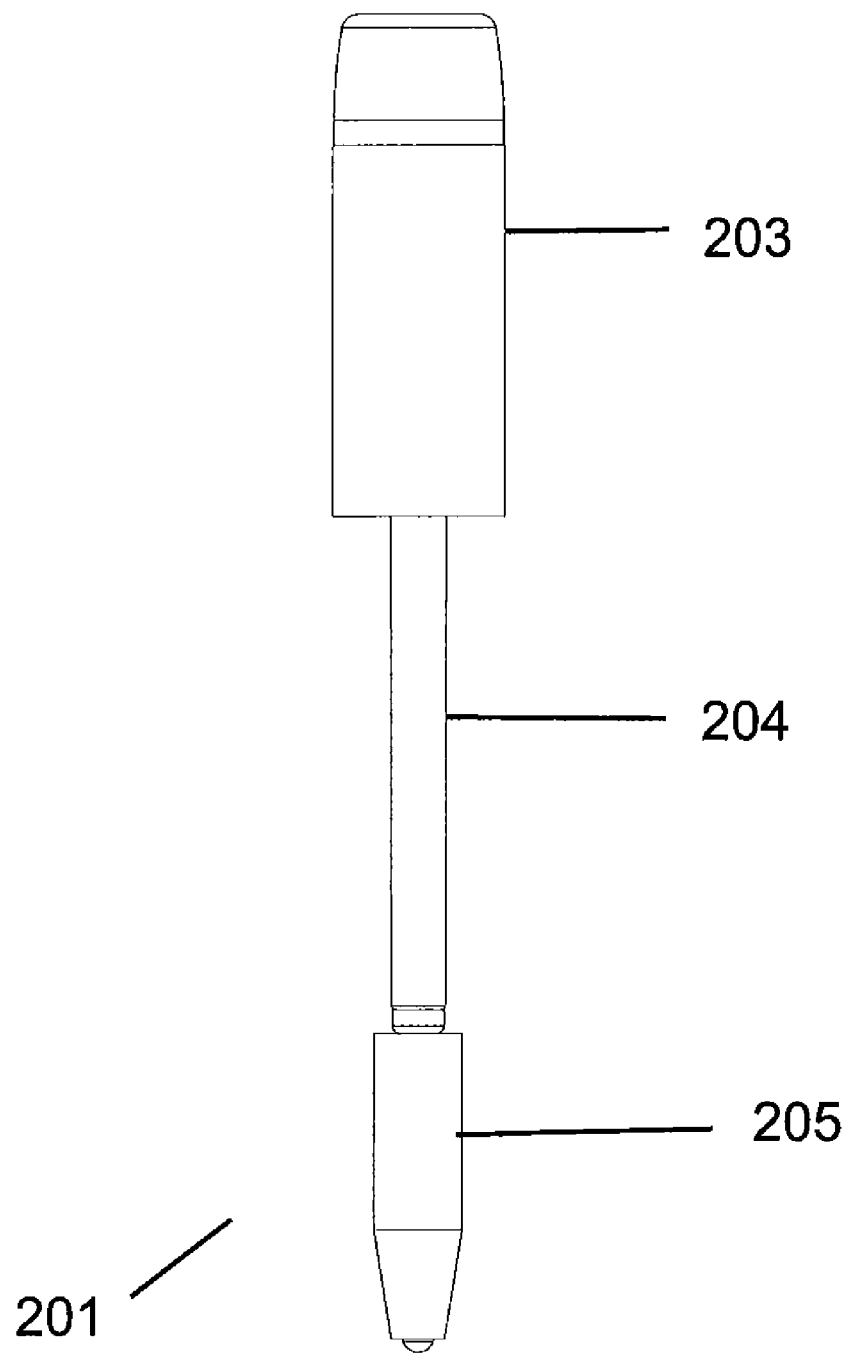
FIG. 6 is an isometric view of the adjustable applicator according to one embodiment of the present invention.
Figure 7:
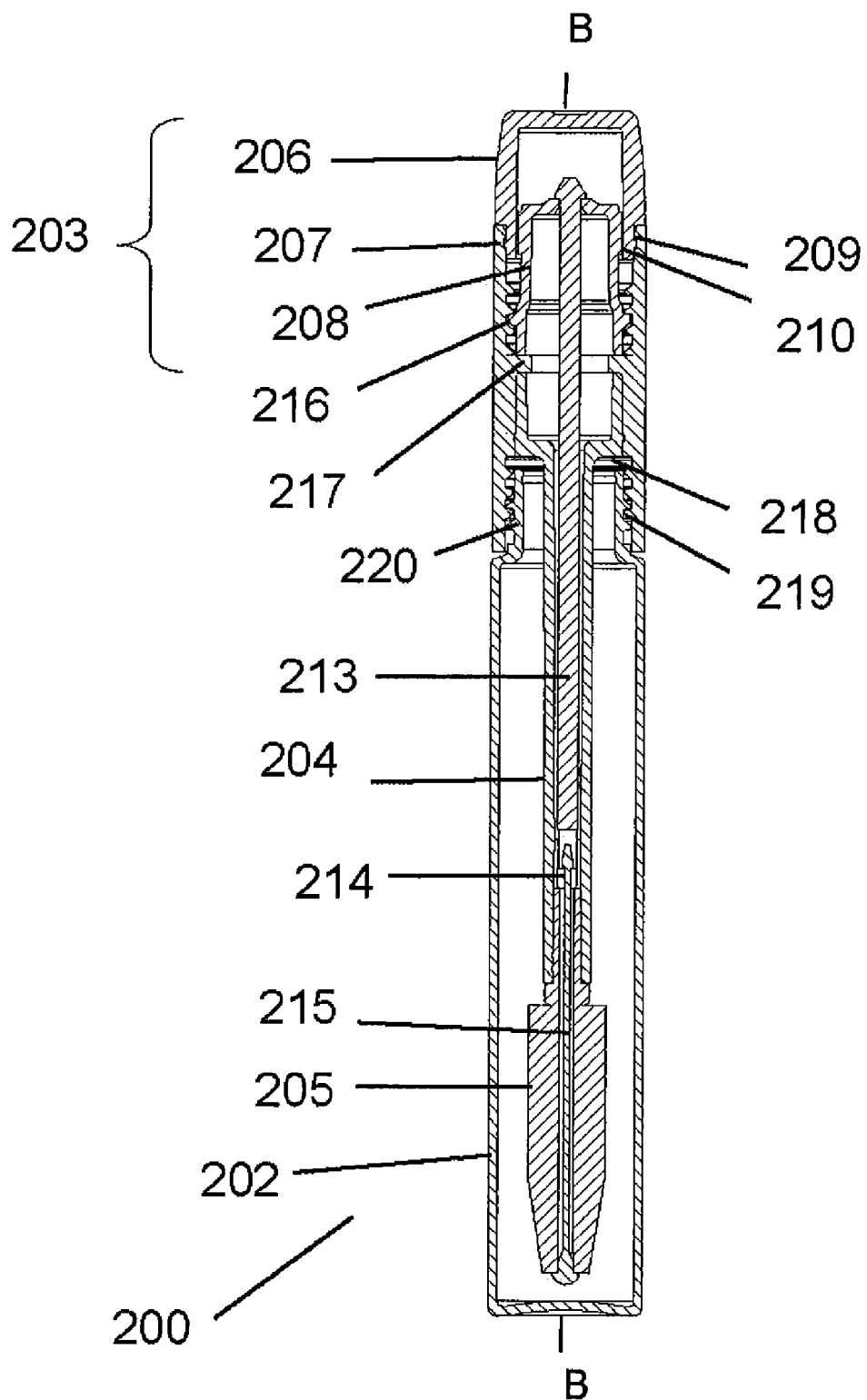
FIG. 7 illustrates a cross-sectional view of the device of FIG. 4.
Figure 8:
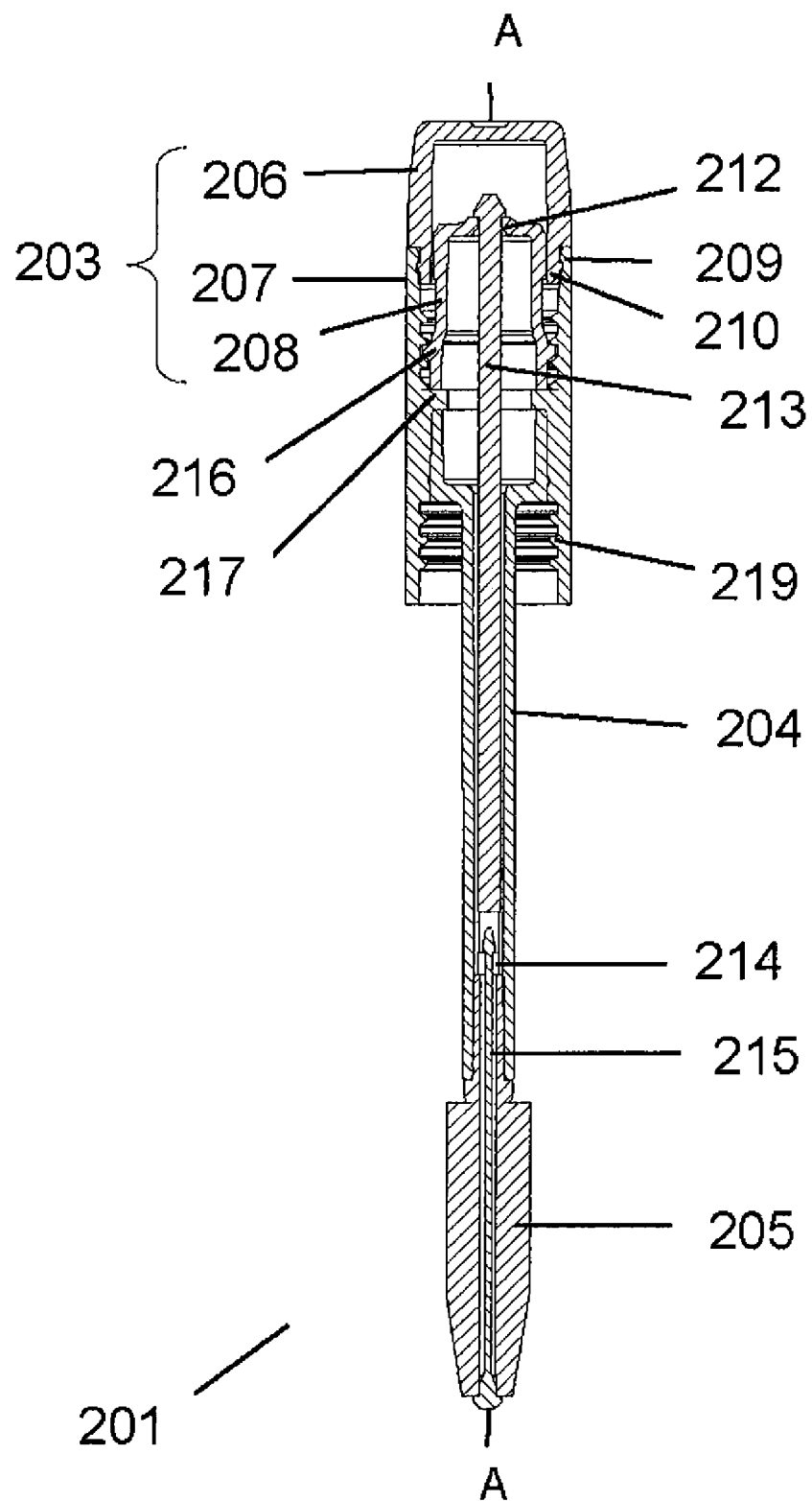
FIG. 8 is cross sectional view of the device of FIG. 6.
Figure 9:
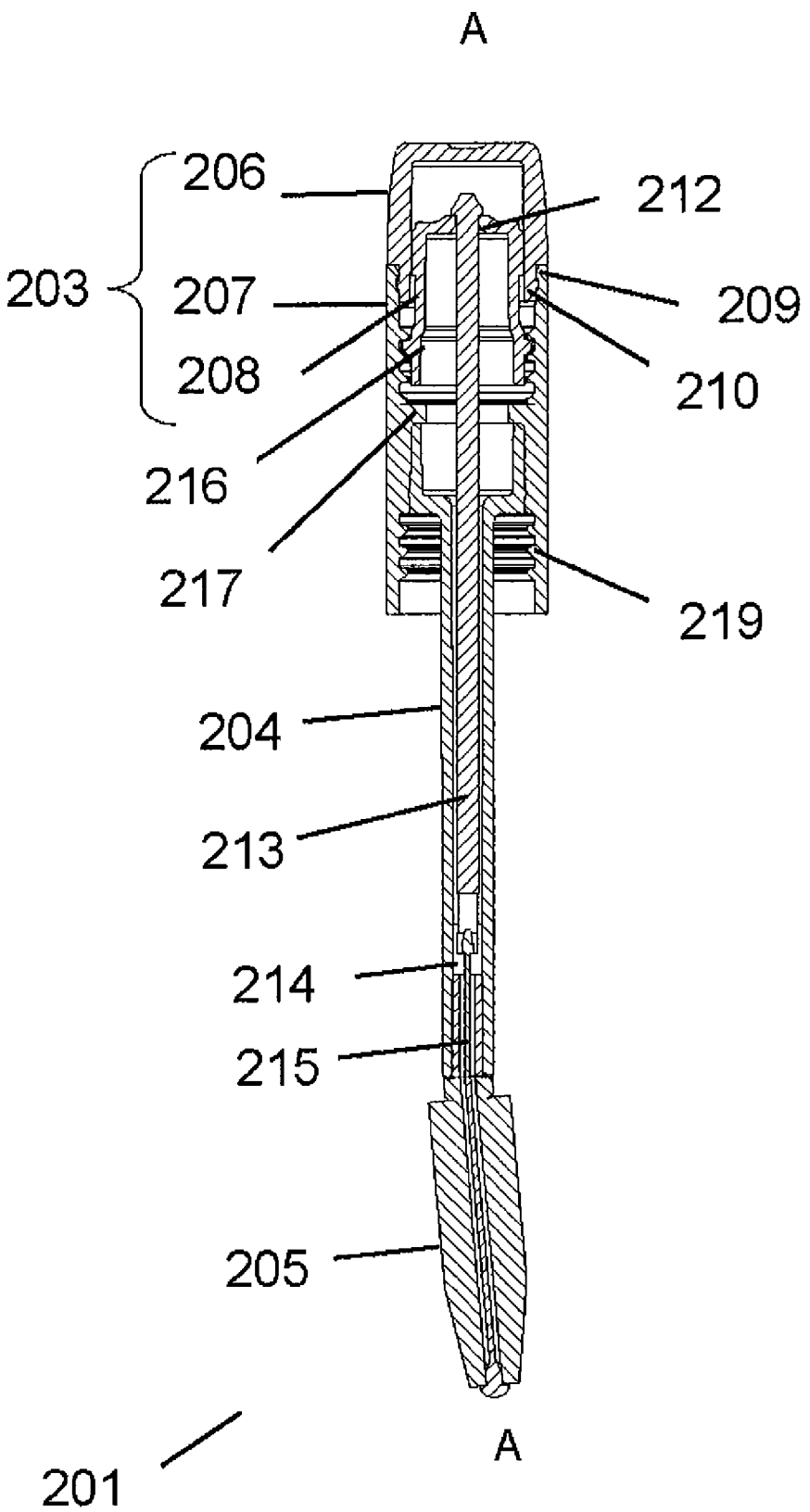
FIG. 9 is cross sectional view of the device of FIG. 6 when the applicator is in curved position; line A-A of FIG. 3.

A device 200 for packaging and dispensing a substance comprising the said applicator is illustrated by FIGS. 4 and 5. The device 200 comprises a gripping means 201 and a receptacle 202 containing the substance. As shown in FIG. 6, the gripping means 201 further comprises a handle 203, a stem 204 and an applicator 205. The proximal end of the stem 204 is connected to the handle 203 while its distal end is connected to the applicator 205. The handle 203 acts as a manipulating means for adjusting the deformation of the applicator 205. The handle 203 further comprises a cap 206 and a casing 207 that houses a movable member 208. FIGS. 6 to 8 illustrate the gripping means 201 in further details and the arrangement of various parts of the device 200. As shown in FIGS. 7 to 9, one end of the casing 207 has ledges 209 which mate with complimentary ledges 210 in the cap 206, thereby restricting movement of the cap 206 along its longitudinal axis and at the same time allowing rotational movement of the cap 206 with respect to the casing 207. However, any lock and key arrangement between the casing and cap could be used for restricting axial movement of the cap with respect to the casing. The movable member 208 is hollow from inside and is so arranged with the cap 206 that its rotational movement with respect to the cap 206 is restricted. The casing 207 has threads 216 in its inner surface just above its centre towards its proximal end that mate with the threads in the movable member 208, thereby allowing movement of the movable member 208 along its axis. Further, below the centre point of casing 207 is present an annular ridge 217 through which it cooperates with the stem 204. Also present are threads 219 at distal end of the casing 207 which cooperate with the threads 220 in the neck of the receptacle 202 helping in fastening and unfastening of the gripping member 201 with respect to the receptacle 202. The stem 204 houses a separate filament 213. However, there may be present one filament that extends through the stem and the applicator element. At the proximal end of the movable member 208 is provided a feature for example a groove 212 to hold one end of the filament 213. The filament 213 has a groove 214 at its distal end which engages the applicator filament 215. The applicator 205 is hollow from inside and houses the applicator filament 215. Also, one end of the applicator filament 215 is fitted inside the applicator 205. The applicator filament 215 is adjusted with the groove 214 such that it is off-centered and provides a favorable and consistent plane along which angular deformation of the applicator occurs. However, the groove 214 may also be centrally aligned. Further, in such an arrangement, the force exerted via the gripping means 201 effects synchronous movement of both the filament 213 in the stem as well as the applicator filament 215 with respect to the applicator 205 to cause the desired angular deformation of the applicator 205. The said device 200 may also include a wiper member 218.

FIG. 9 illustrates the applicator 205 in its angularly deformed state. The rotation of the cap 206 with respect to the casing 207 results in the axial displacement of the movable member 208 thereby displacing the filament 213 and the applicator filament 215 along with it. The displacement in the applicator filament 215 causes the applicator 205 to angularly deform.

During use, the user rotates the cap 206 with respect to the casing 207 of the gripping means to cause the applicator 205 to be suitably deformed along a desired axis. Also, the user can control the magnitude of deformation during use.

Figure 10:
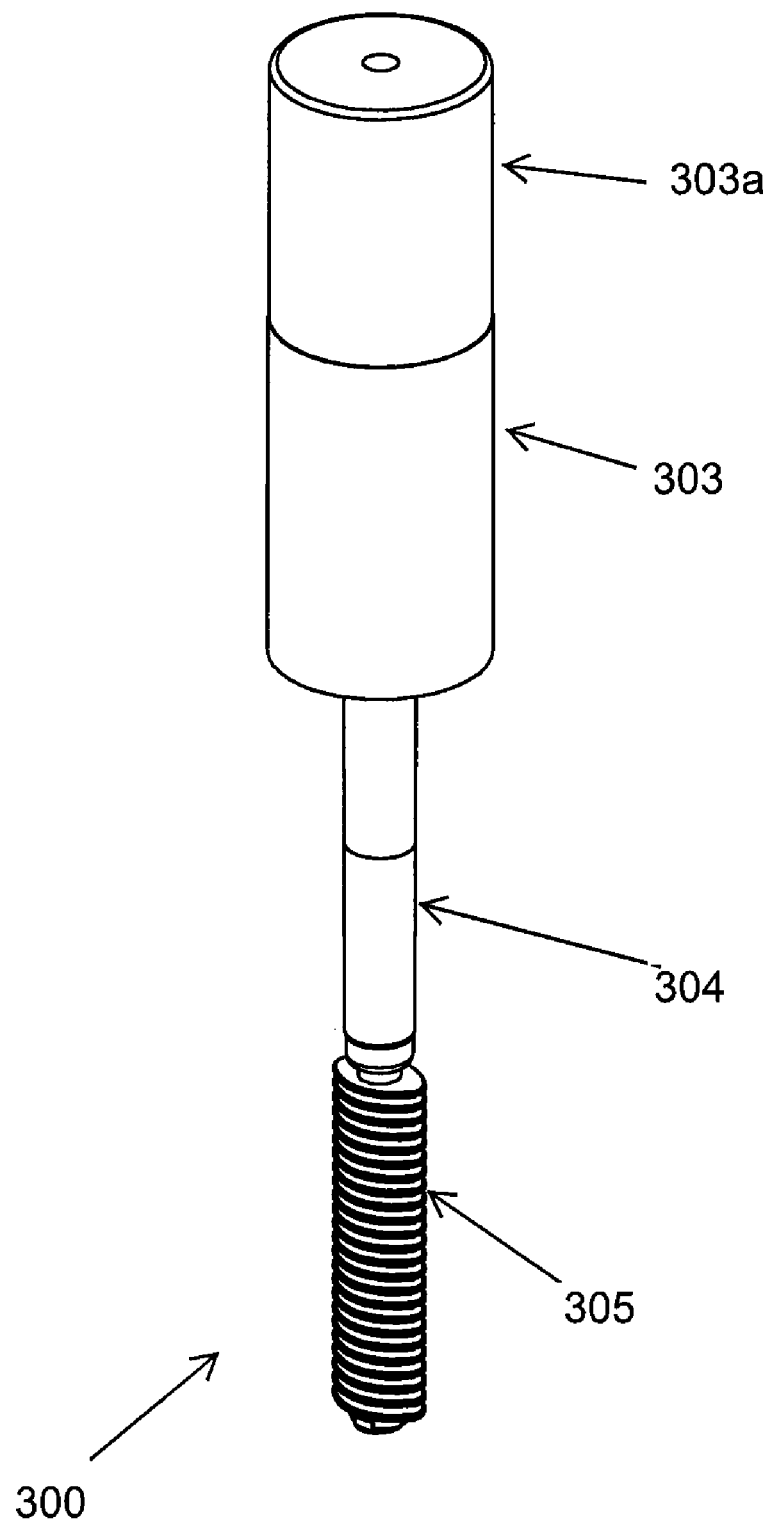
FIG. 10 is an isometric view of an adjustable applicator according to another embodiment of the present invention.
Figure 11:
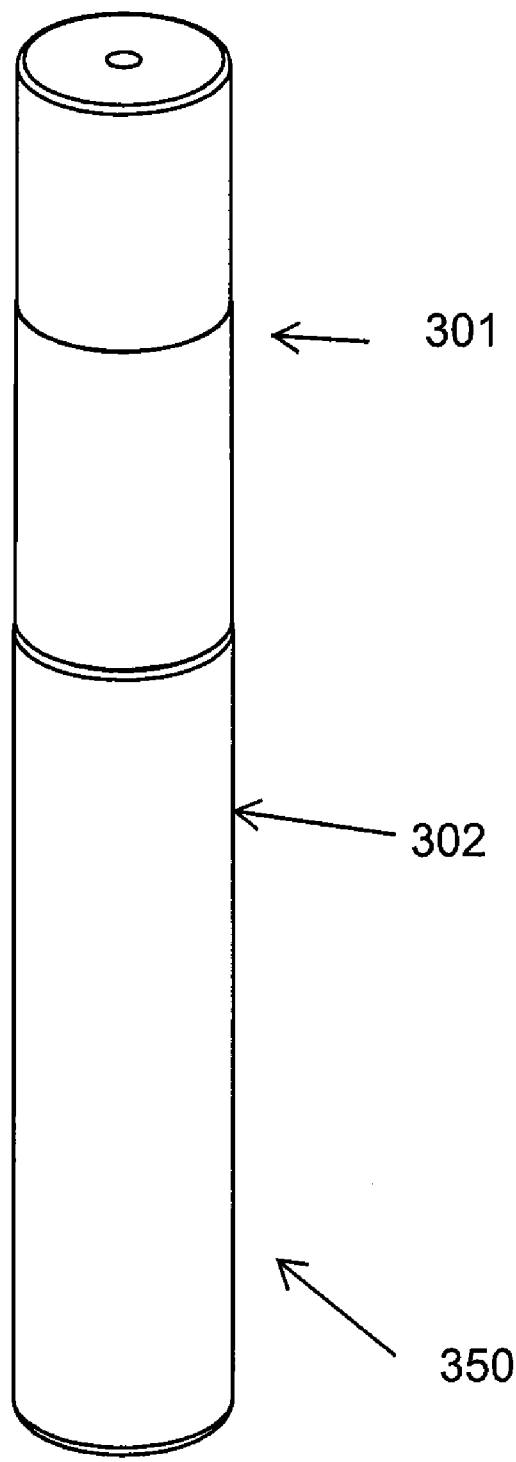
FIG. 11 is an isometric view of the device containing the adjustable applicator of FIG. 10.
Figure 12:
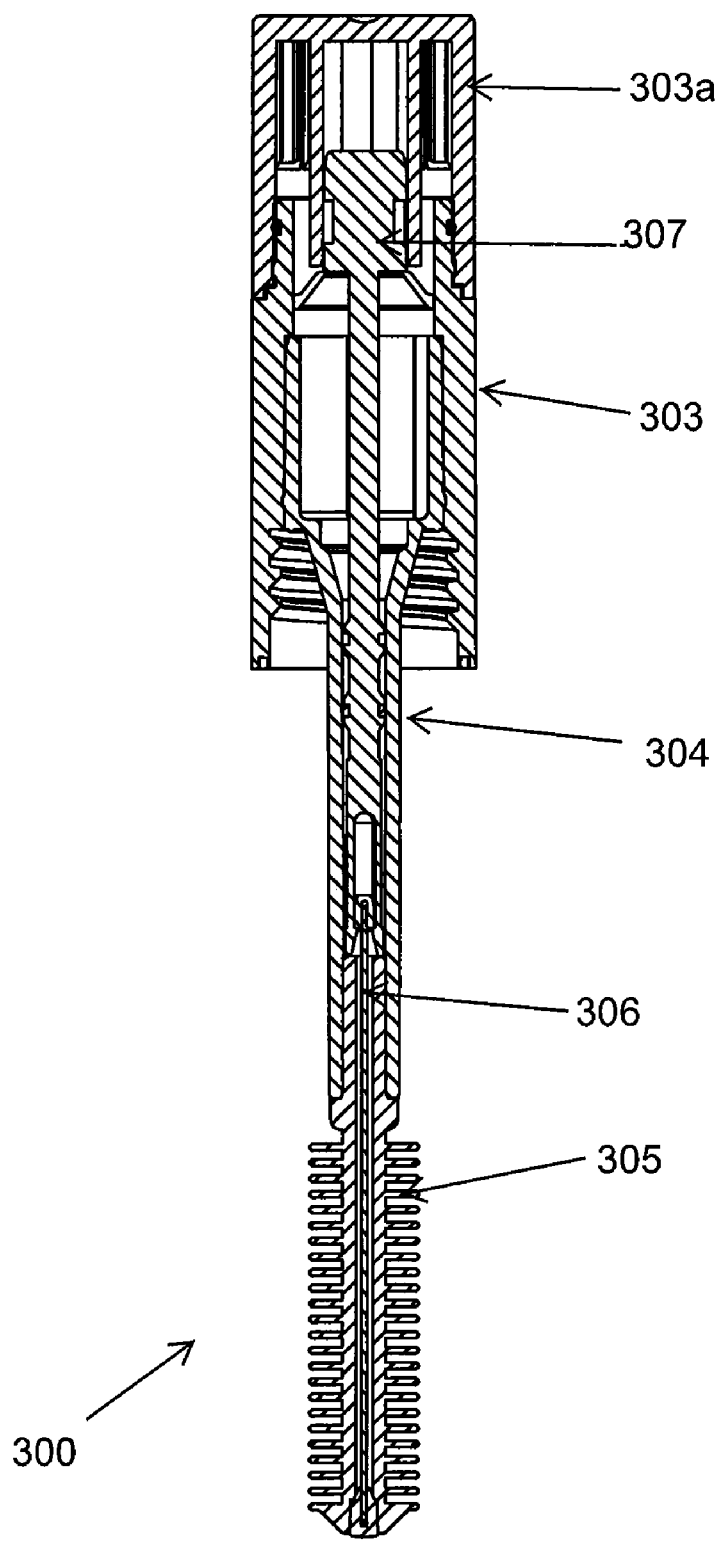
FIG. 12 represents a cross-sectional view of the adjustable applicator of FIG. 10.
Figure 13:
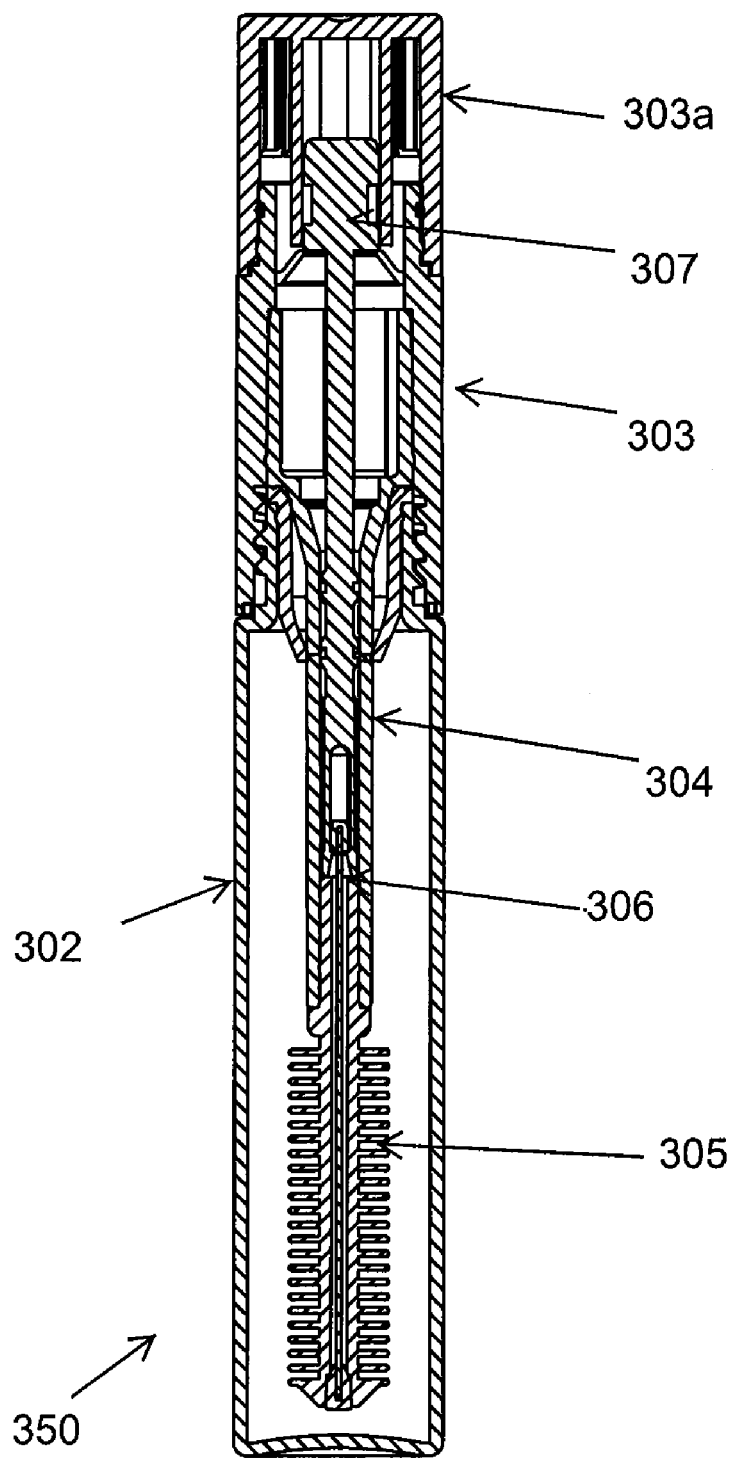
FIG. 13 represents a cross-sectional view of the device of FIG. 11.

FIG. 10 is another embodiment of the present invention showing a device 350 containing an adjustable applicator 300. The device 350 for packaging and dispensing a substance comprising the said adjustable applicator 300 is illustrated by FIGS. 11 to 13. The device 350 comprises a gripping means 301 and a receptacle 302 containing the substance. As shown in FIGS. 10 to 13, the gripping means 301 further comprises a handle 303, a stem 304 and an applicator element 305. In the applicator element 305 is a bore housing an applicator filament 306. The bore may either be centrally or non-centrally aligned. The applicator filament 306 is arranged to be movable inside the bore of the applicator element 305. The applicator element 305 may comprise of bristles, discs or flocked applicator element or any suitable applicator suitable for cosmetic use. Further, the applicator element 305 may be produced from an elastomer or any other elastic material allowing compression and expansion of the applicator. Further, the applicator filament 306 may be made out of a material selected from a polymeric material and metals. The applicator filament 306 is so arranged as to cause progressive angular deformation of the applicator element 305. Further, the applicator element 305 may house a biasing means. Furthermore, the proximal end of the stem 304 is connected to the handle 303 while its distal end is connected to the applicator element 305. The handle 303 acts as a manipulating means for adjusting the angular deformation of the applicator element 305. As shown in FIGS. 11 to 13, the handle 303 of the gripping member 301 further comprises an actuator means 303a which causes the radially-angular deformation in the applicator element 305. The radially-angular deformation being defined herein as the angular deformation occurring on the radial axis of the applicator element. The handle 303 further houses an inner rod 307 such that the inner rod 307 is connected to the actuating means 303a. As seen in FIG. 11, the protrusion in the proximal end of the inner rod 307 sits inside the hollow of the actuating means 303a while the distal end of the inner rod 307 is engaged with the applicator filament 306. Further, the inner rod 307 is encased in the stem 304 of the gripping means 301. Further, the applicator element 305 has a free end 305a and a fixed end 305b such that the fixed end 305b is fixed to the stem 304 of the gripping means 301. As shown in the drawings the applicator filament 306 is housed in the applicator element 305 while the inner rod 307 is housed in the stem 304, however, there may be present one filament that extends through the stem and the applicator element. The distal end of the inner rod 307 is provided a feature for example a groove to hold one end of the applicator filament 306. The applicator element 305 is hollow from inside and houses the applicator filament 306. Also, one end of the applicator filament 306 is fitted inside the applicator element 305. The bore inside the applicator element 305 provides a favorable and consistent plane along which angular deformation of the applicator element 305 occurs. Further, in such an arrangement, the force exerted via the gripping means 301 effects synchronous movement of both the inner rod 307 in the stem 304 as well as the applicator filament 306 with respect to the applicator element 305 to cause the desired angular deformation of the applicator element 305. The said device 350 may also include a wiper member 308. Also present are threads at distal end of the handle 303 which cooperate with the threads in the neck of the receptacle 302 helping in fastening and unfastening of the gripping member 301 with respect to the receptacle 302.

During use, the user rotates the actuating means 303a with respect to the handle 303 of the gripping means 301 to cause the applicator 305 to be suitably angularly deformed at a desired degree. Also, the user can control the magnitude or degree of angular deformation during use.

Figure 14A:
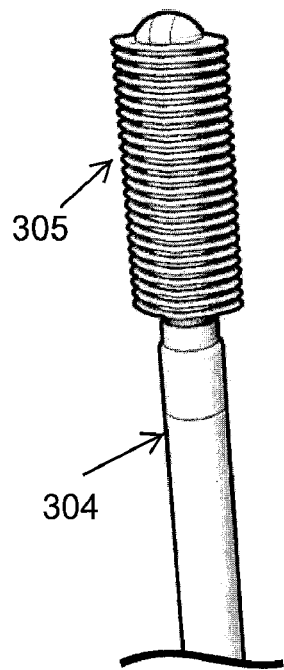
FIG. 14a illustrates the isometric views of the adjustable applicator of FIG. 10.
Figure 14B:
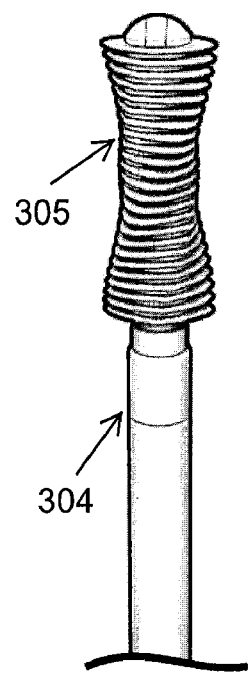
FIG. 14b is an isometric view of the adjustable applicator of FIG. 10 showing the applicator as seen upon 180 degree radially-angular deformation.
Figure 14C:
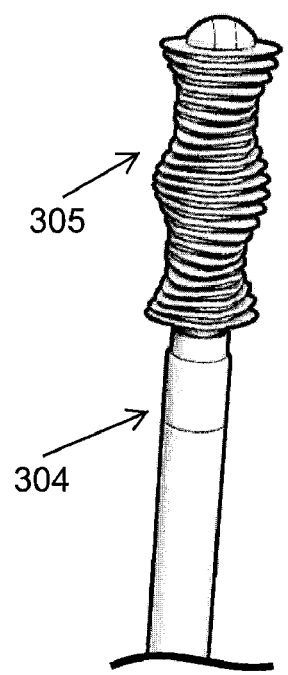
FIG. 14c is an isometric view of the adjustable applicator of FIG. 10 showing the applicator as seen upon 360 degree radially-angular deformation.

FIGS. 14a, 14b and 14c illustrate the isometric view of the applicator 305 in its normal state, deformed state with an angular deformation of 180 degrees and deformed state with angular deformation of 360 degrees respectively. The rotation of the actuating means 303a with respect to the handle 303 results in the synchronous rotation of the inner rod 307 thereby angularly deforming the applicator filament 306 which inn turn causes the applicator 305 to angularly deform. The degree of angular deformation of the applicator filament 306 and hence the applicator 305 depends on the similar force applied to the actuating means 303a. As an exemplary embodiment, when the actuating means 303a is rotated to a less extent, the degree of angular deformation is less in the applicator 305 and if the degree of rotation is high then the degree of angular deformation is higher in the applicator. As represented by FIG. 14b, the degree of angular deformation in the applicator 305 is 180 degrees while in FIG. 14c, the degree of deformation of applicator 305 is 360 degrees.

Figure 15A:
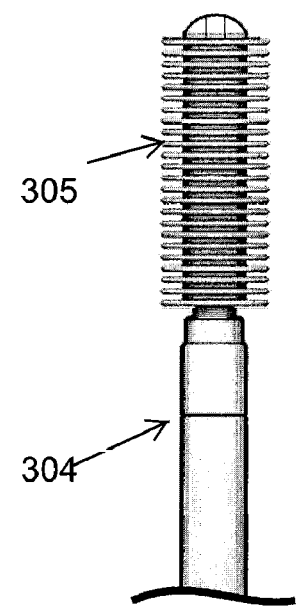
FIG. 15a is a front view of the adjustable applicator of FIG. 10.
Figure 15B:
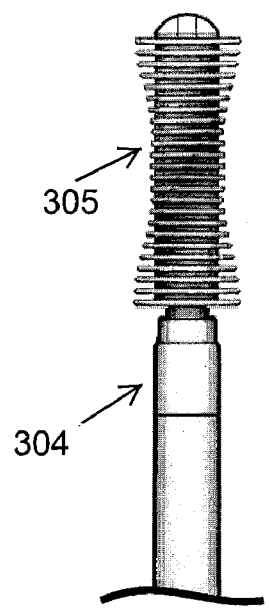
FIG. 15b is a front view of the adjustable applicator of FIG. 10 showing the applicator as seen upon 180 degree radially-angular deformation.
Figure 15C:
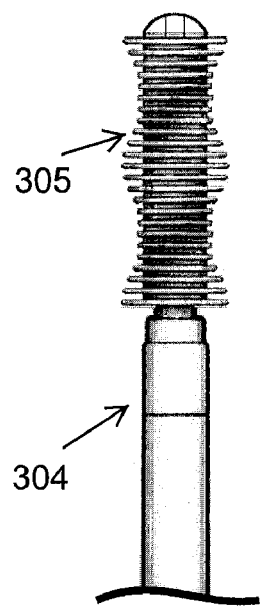
FIG. 15c is an isometric view of the adjustable applicator of FIG. 10 showing the applicator as seen upon 360 degree radially-angular deformation.
Figure 16A:
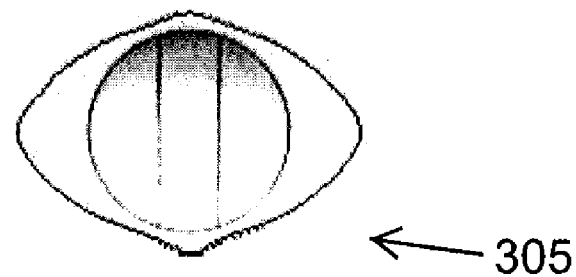
FIG. 16a is a top view of the adjustable applicator of FIG. 10.
Figure 16B:
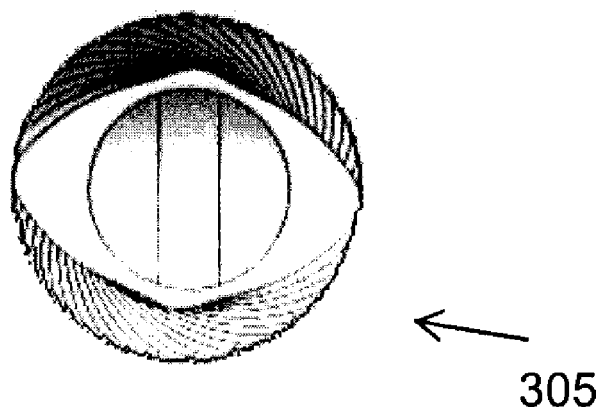
FIG. 16b is a top view of the adjustable applicator of FIG. 10 showing the applicator as seen upon 180 degree radially-angular deformation.
Figure 16C:
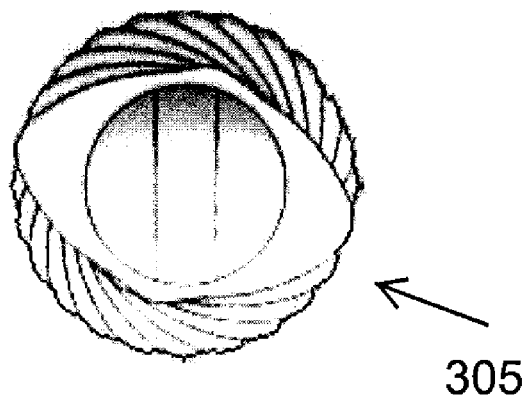
FIG. 16c is a top view of the adjustable applicator of FIG. 10 showing the applicator as seen upon 360 degree radially-angular deformation.

FIGS. 15a, 15b and 15c illustrate the front view of the applicator 305 in its normal state, deformed state with an angular deformation of 180 degrees and deformed state with angular deformation of 360 degrees respectively. While FIGS. 16a, 16b and 16c illustrate the top view of the applicator 305 in its normal state, deformed state with an angular deformation of 180 degrees and deformed state with angular deformation of 360 degrees respectively.

Figure 19A:
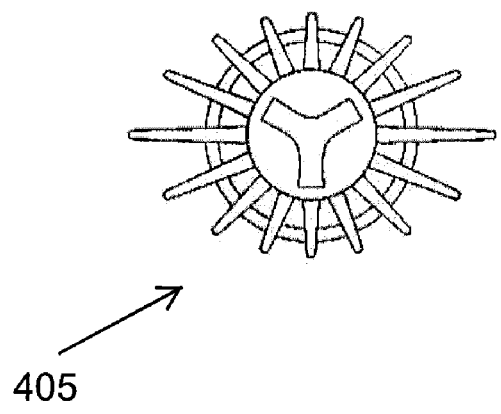
Figure 19B:
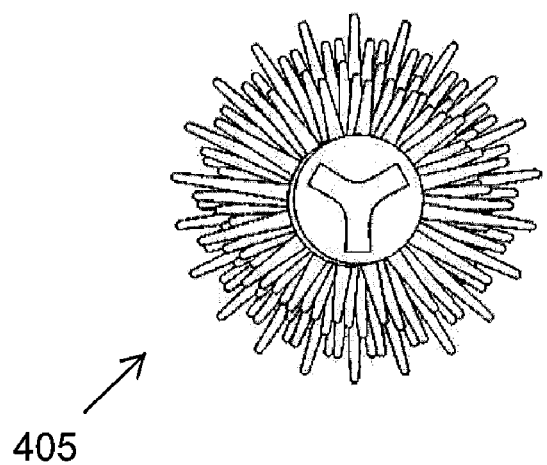
FIG. 19b is a top view of the adjustable applicator of FIG. 17a showing the applicator as seen upon 180 degree radially-angular deformation.
Figure 19C:
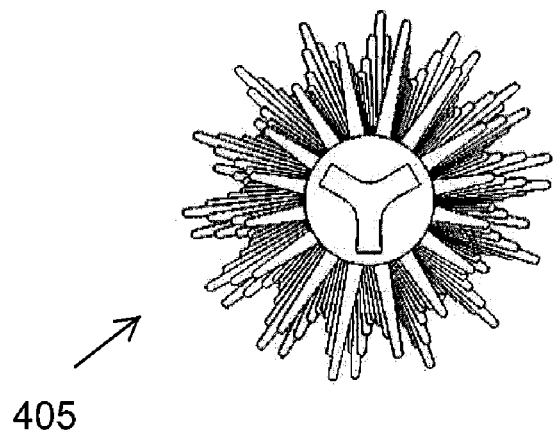
FIG. 19c is a top view of the adjustable applicator of FIG. 17a showing the applicator as seen upon 360 degree radially-angular deformation.

As an exemplary embodiment of the invention, the applicator element 305 may comprise of bristles. FIGS. 17a, 17b and 17c illustrate the isometric view of the applicator 405 in its normal state, deformed state with an angular deformation of 180 degrees and deformed state with angular deformation of 360 degrees respectively. FIGS. 18a, 18b and 18c illustrate the front view of the applicator 405 in its normal state, deformed state with an angular deformation of 180 degrees and deformed state with angular deformation of 360 degrees respectively. While FIGS. 19a, 19b and 19c illustrate the top view of the applicator 405 in its normal state, deformed state with an angular deformation of 180 degrees and deformed state with angular deformation of 360 degrees respectively.

The materials suitable for forming the receptacle 202, 302 and the filament 213 could be polyprolpylene while the cap 203, the casing 207, the movable member 208, the actuating means 303a and the inner rod 307 could be formed of acrylonitrile butadiene styrene or any other suitable polymeric material. The material of applicator filament 215, 306 could be any polymeric material as nylon or could be a suitable metal. The stem 204, 304 may be formed of polyacetal or any other suitable polymeric material. The material for forming wiper 216, 308 could be low-density polyethylene. The aforementioned materials for forming various parts of the device of the present invention are an example, however other suitable materials may also be used.

Depending upon the substance being used in the receptacle, a variety of sizes and shapes of the applicator can be utilized. The applicator 205, 305, 405 may be constructed of a porous or non-porous rubber, fabric mesh, felt material, foamed polymers, sponge material, Hydrel™, TPE or any other suitable material. Also, the applicator could have any suitable shape depending on the kind of application required.

It could have a shape other than cylindrical such as ovular, tapered or any other suitable shape.

Although the above description and drawings show the device being cylindrical, the shapes and profile cross section thereof are not limited to the same.

These and further aspects which will be apparent to the expert of the art are attained by an adjustable applicator in accordance with the main claim.

While the foregoing is directed to embodiments of the present invention, other and further embodiments of the invention may be devised without departing from the basic scope thereof, and the scope thereof is determined by the claims that follow.

What is claimed is:

1. A device for packaging and dispensing a substance comprising a gripping member, a receptacle and a wiper
   wherein said gripping member comprises a handle, a stem having a proximal end and a distal end and an applicator element having a proximal end and a distal end; and
   wherein said applicator element comprises a bore housing a filament, said filament having a proximal end and a distal end; and
   wherein said handle comprises a cap and an actuator means wherein the handle acts as a manipulating means for adjusting the deformation of the applicator element; and
   wherein the proximal end of the stem is connected to the handle while its distal end is connected to the proximal end of the applicator element; and
   wherein said stem of the gripping member has a cavity that houses an inner rod and wherein said inner rod having a proximal end and a distal end; and
   wherein the proximal end of the inner rod is connected to the actuator; and
   wherein the distal end of the inner rod in the stem is operatively connected to the proximal end of the applicator filament; and
   wherein the actuator means of the handle when rotated exerts force to effect synchronous movement of both the inner rod in the stem as well as the applicator filament with respect to the handle, wherein an outer surface of the applicator element is deformed into a helical configuration; and
   wherein the handle has means to help in fastening and unfastening of the gripping member with respect to the receptacle; and
   wherein the distal end of the filament remains attached to the distal end of the applicator element while the out surface of the applicator element into the helical configuration deforms.

* * * * *